(12) United States Patent
DeFrancq et al.

(10) Patent No.: US 6,875,858 B1
(45) Date of Patent: Apr. 5, 2005

(54) FUNCTIONALIZED POLYNUCLEOTIDE COMPOUND, OPTIONALLY MARKED AND METHOD FOR DETECTING A TARGET NUCLEIC ACID

(75) Inventors: Eric DeFrancq, Concelin (FR); Ali Laayoun, Lyons (FR); Jean Lhomme, Meylan (FR); Emmanuelle Trevisiol, Grenoble (FR)

(73) Assignee: Bio Merieux, Marcy L'Etoile (FR)

( * ) Notice: Subject to any disclaimer, the term of this patent is extended or adjusted under 35 U.S.C. 154(b) by 0 days.

(21) Appl. No.: 09/869,796

(22) PCT Filed: Jan. 5, 2000

(86) PCT No.: PCT/FR00/00011

§ 371 (c)(1),
(2), (4) Date: Sep. 19, 2001

(87) PCT Pub. No.: WO00/40590

PCT Pub. Date: Jul. 13, 2000

(30) Foreign Application Priority Data

Jan. 5, 1999 (FR) ............................................. 99 00111

(51) Int. Cl.$^7$ .............................................. C07H 19/04

(52) U.S. Cl. ................... 536/26.6; 536/25.32; 536/26.1

(58) Field of Search ............................ 536/25.32, 26.1, 536/26.6, 22.1, 25.3, 28.1, 28.6, 27, 28, 29, 25.31; 435/6, 91.1, 91.2

(56) References Cited

U.S. PATENT DOCUMENTS

| | | | |
|---|---|---|---|
| 4,828,979 A | * | 5/1989 | Klevan et al. ................. 435/6 |
| 4,981,783 A | | 1/1991 | Augenlicht |
| 5,445,934 A | | 8/1995 | Fodor et al. |
| 5,700,637 A | | 12/1997 | Southern |
| 5,744,305 A | | 4/1998 | Fodor et al. |
| 5,807,522 A | | 9/1998 | Brown et al. |
| 6,222,030 B1 | * | 4/2001 | Dellinger et al. .......... 536/25.3 |

FOREIGN PATENT DOCUMENTS

| | | |
|---|---|---|
| EP | 0 212 951 A2 | 3/1987 |
| EP | 0 254 646 A1 | 1/1988 |
| EP | 0 407 816 A2 | 1/1991 |
| FR | 2 607 507 | 4/1990 |
| WO | WO 86/06726 | 11/1986 |
| WO | WO 92/00989 | 1/1992 |
| WO | WO 93/22326 | 11/1993 |
| WO | WO 95/24185 | 9/1995 |
| WO | WO 95/32980 | 12/1995 |
| WO | WO 98/05766 | 2/1998 |

OTHER PUBLICATIONS

Bergstrom et al. J. Org. Chem. (1981), vol. 46, pp. 1432–1441.*

Kishore N. S. et al., "Comparison of the Acyl Chain Specificities of Human Myristoyl–CoA Synthetase and Human Myristoyl–CoA: Protein N–Myristoyltransferase", The Journal of Biological Chemistry, vol. 268, No. 7, 1993, pp 4889–4902.

Badman et al., "Reactions Between Methiodides of Nucleoside Mannich Bases and Carbon Nucleophiles", J. Chem. Soc., Chem Commun. (1987), (22), 1732–1734.

Bartlett et al., "Transaminations of NN–Dimethylformamide Azine", J. Chem. Soc., 1967, 1664–1666.

Methods in Molecular Biology, vol. 26, "Protocols for Oligonucleotide Conjugates", edited by S. Agrawal, Humana Press, Totowa, New Jersey, 1994.

Wreesmann et al., "Synthesis of short RNA fragments by the benzotriazolyl phosphotriester approach" Nucleic Acids Research, vol. 11, No. 23, (1983), pp 8389–8405.

"Chemistry of Nucleosides and Nucleotides", vol. 3, edited by L. Townsend, Plenum Press, New York and London.

Winn–Deen, PhD, "Automation of Molecular Genetic Methods–Part 2: DNA Amplification Techniques", Journal of Clinical Ligand Assay, vol. 19, No. 1, pp 21–26 (1996).

Ludwig et al., "Rapid and Efficient Synthesis of Nucleoside 5'–O–(1–Thiotriphosphates), 5'–Triphosphates and 2,', 3'–Cyclophosphorothioates Using 2–Chloro–4H–1, 3, 2–benzodioxaphosphorin–4–one", J. Org. Chem., 1989, 54, pp 631–635.

(Continued)

Primary Examiner—James O. Wilson
Assistant Examiner—Patrick Lewis
(74) Attorney, Agent, or Firm—Oliff & Berridge, PLC (57) ABSTRACT

The invention relates to a functionalized compound of general formula (I):

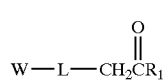

in which
W represents a nucleotide analog,
L represents a linker arm comprising at least four atoms,
$R_1$ represents a linear or branched alkyl chain, A functionalized polynucleotide comprising at least one said compound and a labeled functionalized polynucleotide comprising at least one functionalized compound corresponding to the formula (I').

A method for detecting a target nucleic acid using a said compound is described.

28 Claims, 1 Drawing Sheet

OTHER PUBLICATIONS

Ginot, "Oligonucleotide Micro–Arrays for Identification of Unknown Mutations: How Far from Reality?", Human Mutation, vol. 10, pp 1–10, 1997.

Kozal et al., "Extensive polymorphisms observed in HIV–1 clade B protease gene using high–density oligonucleotide arrays", Nature Medicine, vol. 2, No. 7, pp 753–759, Jul. 1996.

Ramsey, "DNA chips: State–of–the art", Nature Biotechnology, vol. 16, pp 40–44, 1998.

Hobbs, "Palladium–Catalyzed Synthesis of Alkynylamino Nucleosides. A Universal Linker for Nucleic Acids", J. Org. Chem., 1989, 54, pp 3420–3422.

Cheng et al., "Microchip–based Devices for Molecular Diagnosis of Genetic Diseases", Molecular Diagnosis, vol. 1, No. 3, pp 183–200, 1996.

Cheng et al., "Preparation and hybridization analysis of DNA/RNA from E. coli on microfabricated bioelectronic chips", Nature Biotechnology, vol. 16, pp 541–546, 1998.

Ogilvie et al., "The Synthesis of Phosphite Analogues of Ribonucleotides", Tetrahedron Letters, vol. 21, pp 4145–4148, 1980.

Egholm et al., "Peptide Nucleic Acids (PNA). Oligonucleotide Analogues with an Achiral Peptide Backbone", J. Am. Chem. Soc., 1992, 114, pp 1895–1897.

Methods in Molecular Biology, vol. 20, "Protocols for Oligonucleotides and Analogs", edited by S. Agrawal, Humana Press, Totowa, New Jersey, 1993.

"Molecular Methods for Virus Detection", edited by Wiedbrauk et al., Academic Press, San Diego 1995, chapters 8, 9, 12–16.

Nucleic Acid Chemistry, part 2, edited by Townsend et al., John Wiley & Sons, New York, pp 765–766, 1978.

Lipshutz et al., "Using Oligonucleotide Probe Arrays to Access Genetic Diversity", BioTechniques, vol. 19, No. 3, pp 442–447, 1995.

Randolph et al., "Stability, specificity and fluorescence brightness of multiply–labeled fluorescent DNA probes", Nucleic Acids Research, 1997, vol. 25, No. 14, pp. 2923–2929.

Livache et al., "Preparation of a DNA matrix via an electrochemically directed copolymerization of pyrrole and oligonucleotides bearing a pyrrole group", Nucleic Acids Research, 1994, vol. 22, No. 15, pp 2915–2921.

Troesch et al., "*Mycobacterium* Species Identification and Rifampin Resistance Testing with High–Density DNA Probe Arrays", Journal of Clin. Microbiology, vol. 37, No. 1, pp 49–55, Jan. 1999.

* cited by examiner

FIGURE 1

FUNCTIONALIZED POLYNUCLEOTIDE COMPOUND, OPTIONALLY MARKED AND METHOD FOR DETECTING A TARGET NUCLEIC ACID

The present invention relates to a novel nucleoside or nucleotide compound functionalized with an alkyl ketone group, to a polynucleotide comprising at least one nucleotide unit functionalized with an alkyl ketone group, before and after labeling, and also to the implementation and the uses of these products in particular for detecting nucleic acid sequences.

In the nucleic acids field, the synthesis of functionalized nucleotides has been described in particular in the diagnostic field and more particularly for preparing labeled nucleic acid probes which may be used for detecting a target nucleic acid.

Two main types of problem arise in producing these probes. Initially, the functionalized nucleotide must be incorporated into a polynucleotide. Next, the function carried by the nucleotide must be able to react with a tracer in a way which is specific and effective for using the polynucleotide as a detection probe.

Thus, EP-A-0 407 816 describes uracil derivatives modified at position 5 for producing probes via the chemical or enzymatic route. Still with the same aim, patents WO-A-86/06726 and EP-A-0 212 951 describe cytosine derivatives modified at position 4. Patent EP-A-0 254 646 describes an adenosine derivative modified at position 8.

Patent WO-A-92/00989 describes a specific use of modified nucleotides' for introducing proteins onto a polynucleotide.

Patent application WO-A-98/05766 by the applicant, poses the problem of the incorporation of functionalized nucleotides which may be incorporated using enzymatic reaction and in particular using enzymatic amplification techniques, no longer for preparing labeled probes, but directly for generating a labeled target. In this case, there is a greater need for sensitivity and the choice of the functionalized nucleotide is essential for producing the appropriate sensitivity.

A certain number of nucleophilic functions, such as amine and alkoxyamine functions, or electrophilic functions, such as the aldehyde function, are described which allow effective incorporation of the functionalized nucleotide in the course of amplification, but there nevertheless remains a need for a functionalized nucleotide which is even more effective, in particular in terms of ease of preparation, in terms of neutrality with respect to the enzymatic or chemical reactions and in terms of reactivity for the labeling of this nucleotide with a tracer after incorporation.

It has been found, by the applicant, that, surprisingly, the alkyl ketone function answers the abovementioned drawbacks.

In fact, while the prior art describes the use of R—CO— units in which R is an alkyl group, in the case of oligonucleotide synthesis (WO-A-93/22326), the aim of this function is to protect the exocyclic amine of the bases. At the end of synthesis, the amine is deprotected by the action of an alkali agent.

By way of illustration of this state of the art, the following documents may be mentioned. The article by K. K. Ogilvie and M. J. Nemer, Tetrahedron Letters, vol. 21, (1980) pages 4145–4148, discloses, as an intermediate of synthesis of a nucleotide, a nucleotide compound carrying a levulinoyl group attached to the hydroxyl function on the 3' side of the pentose. The aim of introducing this group is to protect the OH function, and it is then immediately removed after said compound has been obtained. The article by C. T. J. Wreesmann et al., Nucleic Acids Research, vol. 11, No 23, (1983) pages 8389–8405, describes the production of a synthetic dinucleotide intermediate, the hydroxyl functions of which are protected by the levulinoyl group. In the presence of aqueous ammonia, the hydroxyl functions are released.

The alkyl ketone function as defined in the present invention is sufficiently stable to withstand this type of treatment and does not therefore represent a protective group, and its stability with respect to the various methods of chemical synthesis results in greater ease of preparation, in particular with respect to amine, aldehyde or alkoxyamine functions, as described in patent WO-A-98/05766.

Similarly, in the abovementioned patents (EP-A-0 407 816, WO-A-86/06726, EP-A-0 212 951, EP-A-0 254 646 and WO-A-92/00989), the functions described for functionalizing the nucleotides are chosen from functions which are reactive from a chemical point of view, such as amine and thiol functions, which are optionally protected. If these functions are protected, a deprotection step is necessary, which complicates the labeling step. If these functions are free, inhibition of the enzymatic reaction or of the side reactions in the case of chemical synthesis may occur.

This chemical stability of the alkyl ketone function should not make it a good candidate for a reaction for coupling to a label, and yet the present invention demonstrates that, surprisingly, this function is reactive with regard to labeling and that, in addition, the detection of the product after labeling is very sensitive.

Finally, the nucleotides carrying this function exhibit excellent neutrality with respect to enzymatic reactions since it is possible to completely replace a natural nucleotide with a nucleotide carrying this alkyl ketone function in an enzymatic reaction, without affecting the yield of this reaction and, even more surprisingly, in certain cases improving it.

Document WO-A-95/24185 describes a nucleoside modified with an alkyl ketone group, the alkyl component of which may comprise up to 20 carbon atoms. This compound is in particular intended for the synthesis of oligonucleotides which find an application in therapy, in diagnosis. The introduction of a group, in particular an alkyl ketone group, onto the pyrimidine nucleus of the nucleoside described is not directed toward functionalization in view of a subsequent reaction of said group, but is aimed at producing oligonucleotide analogs which, with respect to the natural oligonucleotides, exhibit properties which are advantageous in terms of their uses, such as greater ease of hybridization with a target nucleic acid or greater resistance to nucleases.

The object of the present invention is to describe a novel functionalized compound which comprises an alkyl ketone function and which has the formula (I) below:

(I)

in which

W represents a nucleotide analog;

L represents a linker arm between W and the alkyl ketone group, comprising at least four atoms, advantageously at least eight atoms; L is in particular chosen from saturated or unsaturated hydrocarbon-based chains, optionally interrupted by at least one amine, amide or oxy function; preferably, the linker arm comprises a chain of 8 to 30 atoms; in particular, the linker arm comprises from 8 to 20 atoms, at least one of which is an amide function;

R$_1$ represents a linear or branched alkyl chain, preferably an alkyl chain having at most 6 carbons; advantageously, R$_1$ is a methyl group.

The term "nucleotide analog" is intended to mean a nucleoside or a nucleotide, a nucleoside or a nucleotide carrying one or more modifications on one of the constituent elements of said nucleoside or nucleotide, for instance a modification of the deoxyribose or ribose sugar, in particular xylose, arabinose, sugars with an alpha configuration (FR 2 607 507), PNAs (M. Egholm et al., J. Am. Chem. Soc., (1992), 114, 1895–1897), sugar analogs such as 4'-thioribose or -deoxyribose, or sugars with a D or L configuration; a modification of the nitrogen-containing base; a modification of the phosphate or of its equivalent for the nucleotides and also all of the protective groups used in the chemical synthesis.

Advantageously, the compound corresponds to the formula (I) in which W has the general formula (II):

(II)

in which:

R$_2$ represents H or a protective group;

R$_3$ represents H, F, OH, SH, NH$_2$, OCH$_3$ or OR$_5$ in which R$_5$ represents a protective group or an alkyl chain;

R$_4$ represents an H radical, a protective group or a mono-, di- or triphosphate group;

B represents a nitrogen-containing base,

W being attached to L via B.

The nitrogen-containing base is chosen in particular from purines or pyrimidines, such as adenine, guanine, uracil, cytosine or thymine, or any other modified base allowing hybridization, for instance natural modified bases (such as 6-keto purine, xanthine, 5-methylcytosine or 2-aminopurine) or unnatural modified bases (such as thioguanine or 8-oxoguanine, deazapurine or azapurine), or analogs of bases such as universal bases (such as nebularin, nitroindole or nitropyrrole derivatives). Certain functions of the bases likely to interfere with the strategies of solid- or liquid-phase chemical synthesis may be protected with suitable protective groups.

Preferably, the nitrogen-containing base is adenine, uracil or cytosine.

The linker arm L is grafted onto any position of the nitrogen-containing base or of its analog. Preferably, the linker arm will be grafted onto a position which does not disturb hybridization. In particular, the linker arm will be attached to the amine at position 4 of cytosine, position 5 of uracil or the amine at position 6 of adenine.

The term "protective group" is intended to mean the groups conventionally used in the chemical synthesis of nucleosides, nucleotides and oligonucleotides (see, for example, Chemistry of Nucleosides and Nucleotides, Edited by Leroy B. Townsend, Plenum Press, New York and London and Protocols for Oligonucleotides and Analogs, Synthesis and Properties, Edited by S. Agrawal, Humana Press, Totowa, N. J.). Preferably, in the case of chemical synthesis, R$_4$ is a 4,4'-dimethoxytrityl group and R$_2$ is a 2-cyanoethyl-N,N-diisopropylphosphoramidite group and R$_3$ is H or OR$_5$, in which R$_5$ is a protective group used in oligoribonucleotide synthesis.

Preferably, in the case of enzymatic synthesis, R$_4$ is a triphosphate group, R$_2$ is H and R$_3$ is OH.

The phosphate groups are generally in the form of salts, and particularly, lithium, sodium or triethylammonium acetate salts.

The invention also relates to a functionalized polynucleotide comprising at least one functionalized nucleotide as defined above. It may be synthesized by chemical and/or enzymatic reaction. In the case of synthesis by enzymatic reaction, and in particular in the case of enzymatic amplification, the neutrality of the functionalized nucleotide with respect to enzymatic reactions allows the incorporation of several functionalized nucleotides.

The term "enzymatic reaction" includes all reactions in which at least one enzyme with activity which is related to a nucleotide is involved. It is thus intended to mean all reactions comprising at least one enzymatic step in which a nucleotide is used as the substrate for the enzyme, regardless of whether said nucleotide is transformed during this enzymatic step. By way of example, such reactions are chosen from those used in molecular biology techniques such as transcription, ligation, elongation and cleavage and more particularly in amplification techniques (see, for example, the article by E. Winn-Deen, Journal of Clinical assay, vol 19, p21–26, (1996)).

Thus, the enzymes which have activities which are related to nucleotides may, in particular, be selected from the following nonexhaustive list: DNA-dependent DNA polymerases, such as the DNA polymerase I Klenow fragment of E. Coli, TAQ polymerase, the T7, T4 or T5 DNA polymerases, eukaryotic cellular polymerases or viral polymerases; RNA-dependent DNA polymerases, such as AMV (avian myoblastosis virus) or MMLV (Moloney murine leukemia virus) polymerases; RNA polymerases, such as the T7, T3 SP6, N4, or PBSII RNA polymerases, or E. Coli RNA polymerase; enzymes with nuclease activity, such am restriction endonucleases or Rnase H; or polyA polymerases, replicases such as Q-beta-replicase, terminal transferases or ligases.

Heat-stable enzymes which have the enzymatic activities described above may also be used in the invention.

According to a preferred embodiment, techniques using a transcription step, such as NASBA (nucleic acid sequence based amplification), TMA (transcription mediated amplification) or post-PCR (polymerase chain reaction) transcription, as described in the articles by R. J. Lipshutz et al, Biotechniques, 19(3), p442–447, 1995 or M. Kozal et al, Nature Medecine, 2(7), p753–759, 1996, will be chosen for the synthesis of the functionalized polynucleotide.

The elements and conditions required for carrying out these enzymatic reactions so as to produce a polynucleotide are well known to those skilled in the art. The manual Current Protocols in Molecular Biology, edited by F. M. Ausubel, R. Brent, R. E. Kingston, D. D. Moore J. G. Seidman, J. A. Smith and K. Struhl, John Wiley & Sons, 1996 volume 1 chapter 3, gives the methods for enzymatic manipulation of DNA and RNA. Similarly, the work "Molecular Methods for Virus Detection", edited by D. L. Wiedbrand and D. H. Farkas, Academic press, San Diego, 1995 in particular in chapters 8, 9, 12, 13, 14, 15 and 16, gives examples for the enzymatic amplification techniques.

The term "chemical synthesis" is intended to mean all methods, both in solid phase and in liquid phase, in which a suitably protected nucleotide monomer reacts with another nucleotide monomer or polymer via a coupling reaction.

Chemical synthesis methods are given, for example, in "Methods in Molecular Biology, volume 20, Protocols for oligonucleotides and analogs", edited by S. Agrawal, Humana Press, Totowa, N.J., 1993 and "Methods in Molecular Biology, volume 26, Protocols for oligonucleotides conjugates", edited by S. Agrawal, Humana Press, Totowa, N.J., 1994.

The term "polynucleotide" is intended to mean a chain of at least 2 nucleotide monomers. Preferably, if the polynucleotide is synthesized by the chemical route, it is less than 300 nucleotides, and advantageously less than 150 nucleotides, in size. Preferably, if the polynucleotide is synthesized by enzymatic reaction, it is less than 20 kb, and advantageously less than 10 kb, in size.

The two routes of synthesis, chemical synthesis and enzymatic synthesis, can be combined in order to prepare a polynucleotide.

The invention also relates to a labeled functionalized polynucleotide comprising at least one functionalized compound of general formula (I'):

W-[-L-]$_n$-CH$_2$COR$_1$.    (I')

in which
W represents a nucleotide analog as defined above,
L represents a linker arm comprising at least four atoms,
n represents an index equal to 0 or 1,
R$_1$ represents a linear or branched alkyl chain, the alkyl ketone group of said functionalized compound having interacted with a labeling reagent.

W, L and R$_1$ advantageously satisfy the definitions given above to describe preferred functionalized compounds of the invention.

The term "labeling reagent" is intended to mean a tracer which directly or indirectly generates a detectable signal capable of reacting with the alkyl ketone function.

The following is a nonlimiting list of these tracers:

enzymes which produce a signal detectable, for example, by colorimetry, fluorescence or luminescence, such as horseradish peroxidase, alkaline phosphatase, beta-galactosidase or glucose-6-phosphate dehydrogenase;

chromophores, such as fluorescent, luminescent or dye compounds;

groups with an electron density which can be detected by electron microscopy or through their electrical property, such as by conductivity, amperometry, voltametry, impedance measurements;

groups which can be detected using optical methods, such as diffraction, surface plasmon resonance or contact angle variation, or physical methods, such as atomic force spectroscopy, the tunnel effect;

radioactive molecules such as $^{32}$P, $^{35}$S or $^{125}$I.

Preferably, the tracer is a fluorescent compound with low steric hindrance, such as fluorescein, dansyl, chromophores of the IR (Li-COR Inc, Lincoln Nebr., USA), CY5 and CY3 (Randolph J. B. and al, Nucleic Acids Res., 25(14), p2923–2929, 1997) type and derivatives thereof. The term "low steric hindrance" is intended to mean a molecular weight of less than 1000 g/mol.

In order to react with the alkyl ketone function, this labeling reagent must carry a nucleophilic function capable of reacting with an alkyl ketone function, such as alkoxyamine or hydrazine functions.

Preferably, the function chosen is alkoxyamine, which may be introduced by any direct or indirect means. The term "direct means" is intended to mean a covalent bond between the tracer, or a molecule carrying the tracer, and the alkoxyamine function. The term "indirect means" is intended to mean complexation systems of the metal/chelate type or affinity systems, i.e. haptens which can be detected by a specific antibody or a protein, such as the biotin/avidin or streptavidin pairing or the sugar/lectin pairing. In this case, the tracer is carried by the antibody or the protein and the alkoxyamine function is carried by the hapten.

In particular, the labeling reagent has the formula:

The invention also relates to a solid support to which a nucleotide, a nucleoside or a polynucleotide according to the invention is attached by covalence.

In order to perform this attachment, a nucleotide, a nucleoside or a polynucleotide comprising an alkyl ketone group is reacted with a solid support on which there is an alkoxyamine or hydrazine function, preferably an alkoxyamine function.

In a first embodiment, the polynucleotide is preformed and the final reaction consists in grafting, at a predetermined position on the support, the polynucleotide. In one particular embodiment, the polynucleotides are synthetic oligonucleotides (synthesized via the chemical route) which are short in size (less than 50 bases), and in a second particular embodiment, the polynucleotides are more than 50 bases in size and are prepared using enzymatic methods such as enzymatic amplification.

In a second embodiment, the nucleoside or nucleotide is added via successive steps (chain extension) on the support in order to obtain, at the end of the synthetic cycle, a polynucleotide grafted to a predetermined position on the solid support.

A preferential use of these grafted supports is the production of biochips for gene analysis.

By way of illustration, examples of these biochips are given in the publications by G. Ramsay, Nature Biotechnology, 16, p40–44, 1998; F. Ginot, Human Mutation, 10, p1–10, 1997; J. Cheng et al, Molecular diagnosis, 1(3), p183–200, 1996; T. Livache et al, Nucleic Acids Research, 22(15), p2915–2921, 1994; J. Cheng et al, Nature Biotechnology, 16, p541–546, 1998 or in patents U.S. Pat. No. 4,981,783 (Augenlicht), U.S. Pat. No. 5,700,637 (Southern), U.S. Pat. No. 5,445,934 (Fodor), U.S. Pat. No. 5,744,305 (Fodor), U.S. Pat. No. 5,807,522 (Brown).

The invention also relates to a method for detecting a target nucleic acid in a sample, in which this target nucleic acid, optionally pretreated, is brought into contact with at least one functionalized compound corresponding to formula (I'), in the presence of the elements and under conditions required for producing a polynucleotide of the invention, so as to produce a functionalized polynucleotide; in labeling said polynucleotide with a labeling reagent and then in detecting said labeled polynucleotide. The above-mentioned elements and conditions are well known to those skilled in the art.

The term "pretreatment" is intended to mean the various steps for treating the sample in order to make the target nucleic acid accessible, such as for example lyzing, fluidifying, concentrating.

Preferably, the functionalized polynucleotide is obtained via an enzymatic amplification reaction which acts on the target nucleic acid which serves as a matrix, and which is capable of incorporating the functionalized nucleotide.

Advantageously, the enzymatic amplification technique is NASBA (nucleic acid sequence based amplification), TMA (transcription mediated amplification) or post-PCR (polymerase chain reaction) transcription, as described in the articles by R. J. Lipshutz et al, Biotechniques, 19(3), p442–447, 1995 or M. Kozal et al, Nature Medecine, 2(7), p753–759, 1996.

The labeled polynucleotide may be detected qualitatively and/or quantitatively in homogeneous or heterogeneous phase. A preferential detection mode consists in attaching the labeled polynucleotide to a solid support via a hybridization reaction between the labeled polynucleotide and another polynucleotide, itself attached to the solid support, and then revealing the presence of the labeled polynucleotide after a washing step. This revelation is carried out directly by reading, such as for example with a scanner or a camera if the tracer is a fluorescent molecule.

The detection method is particularly useful when a multitude of polynucleotides are attached to the solid support at a predetermined position so as to form a "DNA chip".

Specifically, the density of the polynucleotides attached to the solid support imposes considerable steric constraints during the hybridization and the labeled polynucleotide according to the invention allows good sensitivity of detection. Examples of these chips are given, for example cited in the publications and patents mentioned above.

The detection method can be used for sequencing, profiling the expression of messenger RNAs or screening mutations, or diagnosing infectious or genetic diseases.

A fragmentation step can take place in order to promote the hybridization of the labeled polynucleotide on the DNA chip, before, together with, or after the labeling step.

The invention also relates to a method for detecting a target nucleic acid in a sample, in which this target nucleic acid is brought into contact with a functionalized polynucleotide of the invention, the labeling reagent is reacted and the presence of the target nucleic acid is detected.

Another means of carrying out the invention is to react the functionalized polynucleotide and the labeling reagent, before the hybridization with the target nucleic acid. This target nucleic acid may have been amplified using an enzymatic amplification technique.

Finally the invention relates to the method for detecting a target nucleic acid, according to which a labeled polynucleotide of the invention is available for use, the nucleic acid is brought into contact with the labeled polynucleotide and the presence of the target nucleic acid is detected.

The term "solid support" as used herein includes all materials on which it is possible to immobilize a polynucleotide for use in diagnostic tests and in separation processes. Natural or synthetic materials, which may or may not be chemically modified, may be used as a solid support, in particular polysaccharides such as cellulose-based materials, for example paper, cellulose derivatives such as cellulose acetate and nitrocellulose, dextran; polymers such as polyvinyl chlorides, polyethylenes, polystyrenes, polyacrylates, polyamides, or, copolymers based on monomers of the styrene type, unsaturated carboxylic acid esters, vinylidene chloride, dienes or compounds with nitrile functions (such as acrylonitrile); vinyl chloride/propylene copolymers, vinyl chloride/vinyl acetate copolymers; natural fibers such as cotton and synthetic fibers such as nylon; inorganic materials such as silica, quartz, glasses, ceramics; latexes, i.e. colloidal aqueous dispersions of any water-insoluble polymer; magnetic particles; metallic derivatives, gels etc.

The following examples make it possible to illustrate some of the advantages of the invention without, however, limiting the scope thereof.

The attached FIGURE represents the transcription yields measured as a function of the nucleotide used.

EXAMPLE I

Synthesis of Methyl Ketone Nucleotides

I.1. Synthesis of uridine(C5)—C9-methylketone 1

1

Synthetic pathway:

The 2',3'-OH positions are protected by reacting acetone in acid medium according to the protocol described in "Nucleic acid chemistry, Editors Townsend-Tipson, Wiley-Interscience, John Wiley & Sons, p 765–766 (1978)".

Synthesis of the Methyl Ketone Chain

The methyl ketone unit is introduced onto the arm by peptide coupling between propargylamine and 6-oxo-heptanoic acid.

6-Oxoheptanoic acid (2.75 g, 18.16 mmol) is solubilized in 40 ml of anhydrous THF. The solution is placed at 0° C. under an argon atmosphere. N-methyl-, morpholine (2 ml, 18.16 mmol) is then added, followed by propargylamine (1.25 ml, 18.16 mmol) 15 min later, and the mixture is allowed to return to room temperature. After reaction for 30 minutes, the precipitate is filtered and evaporated to dryness.

The residue obtained is taken up in dichloromethane and is washed with a 0.1 N aqueous sodium hydroxide solution, then with a 1 N aqueous hydrochloric acid solution and finally with water saturated with sodium chloride.

After drying over Na$_2$SO$_4$, the dichloromethane is evaporated off and the residue is chromatographed on silica gel (eluent: ethyl acetate). The product is thus obtained in the form of a white powder (2.6 g, 14.4 mmol; 80%).

The methyl ketone chain was characterized by proton NMR, carbon 13 NMR and mass spectrometry.

*Introduction of the methyl ketone chain onto the nucleoside: Heck coupling* (Hobbs, J. Org. Chem., 1989, 54, 3420–3422)

5-Iodouridine 2',3'-isopropylidene (500 mg; 1.22 mmol) and copper iodide (44 mg, 0.232 mmol) are added to 5 ml of DMF which has been degassed and placed under argon. The reaction is placed in darkness and then triethylamine (323 μl, 2.32 mmol) and the chain containing the methyl ketone function (630 mg, 3.48 mmol) are added.

The mixture is left under argon for 10 minutes. Tetrakis triphenylphosphine palladium (134 mg, 0.116 mmol) is then added. After reaction for 3 hours, the DMF is evaporated off, followed by coevaporation with acetonitrile. The residue is taken up in ethyl acetate and the organic phase is washed with an aqueous solution saturated with sodium chloride. After drying over $Na_2SO_4$ and evaporation, the residue is chromatographed on silica gel (eluent: ethyl acetate/methanol: 90/10).

After evaporation, the methyl ketone nucleoside is obtained in the form of a whitish powder (340 mg., 0.73 mmol, 60%). The product was characterized by proton NMR, carbon 13 NMR and mass spectrometry. The methyl ketone nucleoside correctly protected for the introduction of the triphosphate in 5' is thus obtained.

Production of the Uridine(C5)—C9-Methylketone Triphosphate Nucleoside 1

*Phosphorylation: Eckstein, J. Org. Chem.,* 1989, 54, 631–635

The methyl ketone nucleoside (46 mg, 0.1 mmol) is dissolved in anhydrous pyridine and evaporated twice. 100 ml of pyridine/300 ml of dioxane and a freshly prepared solution of 2-chloro-4H-1,2,3-dioxaphosphorin-4-one (1 M) in dioxane (130 µl; 130 mmol) are then added under argon, the mixture is left to stir for 20 minutes, and then a 0.5 M solution of tributylammonium pyrophosphate in anhydrous DMF (320µl, 0.16 mmol) and, simultaneously, 130 µl of tributylamine are then added. After 30 minutes, 2 ml of 1% iodine solution are added to a pyridine/water (98/2: v/v) mixture.

After stirring for 20 minutes, the excess iodine is eliminated with a 5% aqueous $NaHSO_3$ solution and the stirring is continued for 10 minutes. The mixture is evaporated to dryness and an extraction is carried out with a water/dichloromethane mixture. The aqueous phase is evaporated off and then C18 reverse phase chromatography (flash) is performed (eluent: water/methanol 1/1). The fractions containing the product are evaporated and the counter-ion exchange is carried out by passing over Dowex, Na+ resin. The protected triphosphate is thus recovered (0.03 mmol; 30%).

Deprotection

The protected triphosphate (0.03 mmol) is taken up in 15 ml of milli-Q water to which 15 ml of a 25% aqueous TFA solution are added. The solution is stirred for 15 minutes, then evaporated and coevaporated twice with water.

The product is taken up in 10 ml of milli-Q water and neutralized with 0.1 N sodium hydroxide, to pH 8. After the evaporation, the protected triphosphate is purified on C18 reverse phase ($H_2O$ then HMO/MeOH, 1/1). The counter-ion exchange is carried out by passing over cation exchange resin (Dowex $Na^+$). The fractions containing the product are evaporated and assayed. 0.021 mmol (70%) of the uridine (C5)-C9-methylketone triphosphate nucleoside 1 is thus recovered, and this nucleoside was characterized by proton NMR, carbon 13 NMR and phosphorus 31 NMR.

I.2. Synthesis of Adenosine(N6)—C10-Methylketone 2

1

Synthetic Pathway

The introduction of diaminobutane at position 6 of the adenosine is carried out by substitution of the triazolo group carried by the protected intermediate nucleoside. The methyl ketone function is then introduced by peptide coupling at the nucleoside level. After deprotection of the silyl group in 5', phosphorylation is carried out by the Eckstein method. After deprotection, the expected triphosphate is obtained, which is characterized by proton NMR and phosphorus 31 NMR.

Synthesis of the Protected Triazolo Nucleoside

*Preparation of adenosine 2',3'-Isopropylidene*

(Nucleic Acid Chemistry, part 2, Editors Townsend, Tipson, Wiley Interscience, John Wiley & Sons p. 768, (1978))

Ethyl orthoformate (12.44 ml, 74.8 mmol) is added dropwise, under argon, to a suspension of adenosine (5 g, 18.7 mmol) in acetone (10 ml) containing APTS (para-toluene-sulfonic acid) (3.9 g, 20.6 mmol). After reaction overnight, 110 ml of water containing 1.86 ml of aqueous ammonia at 27% are added. After stirring for 30 minutes, the reaction mixture is evaporated until white crystals appear. After 12 h at +40° C., a white precipitate is obtained which is recrystallized in water. 4.17 g (13.5 mmol, 72%) of product is obtained in the form of a white powder. This intermediate was characterized by proton NMR.

Synthesis of amidine (Bartlett and Humphreg, J. Chem. Soc., 1967, 1664–1666)

Thionyl chloride (39.96 g, 24.5 ml, 0.338 mol) is added dropwise to N—N'-diformylhydrazine (12 g, 0.136 mol) in DMF (270 ml) at 10° C. The mixture becomes yellow. Stirring is maintained for 2 days. The precipitate obtained is filtered and washed with DMF then with ether. After drying under a vacuum, the amidine is obtained with a yield of 95% (28 g, 0.130 mol).

Preparation of the triazolo intermediate (Samano, Miles, Robins, J. Am. Chem. Soc., 1994, 116, 9331–9332)

The adenosine isopropylidene (1 g, 3.2 mmol) and the amidine described above (1.4 g, 6.5 mmol) are stirred into pyridine (15 ml) at 100° C. under argon for 48 h. The pyridine is then evaporated off and coevaporated with toluene. The oil obtained is then taken up with ethyl acetate and this organic phase is washed with water saturated with NaCl. After drying over $Na_2SO_4$ and evaporation, the triazolo nucleoside is obtained in the form of a white powder with a yield of 60% (700 mg, 1.9 mmol). It was then characterized by proton NMR.

Protection in 5' of the Triazolo Derivative

The triazolo nucleoside (1 g, 2.8 mmol) is solubilized in 20 ml of pyridine. TBDMS-Cl (tert-butyldimethylsilyl chloride), (462 mg, 3 mmol) is added at 0° C. under argon. Stirring is maintained for two hours then the pyridine is evaporated off. The residue thus obtained is chromatographed on silica gel (eluent: $CH_2Cl_2$/methanol 95/5). After evaporation, the totally protected intermediate adenosine is obtained in the form of a white powder (1.25 mg, 2.6 mmol, 93%). This nucleoside was characterized by proton NMR, carbon 13 NMR and mass spectrometry.

Introduction of the Diaminobutane Chain onto the Protected Intermediate Adenosine The triazolo adenosine (1.25 mg, 2.64 mmol) is solubilized in 10 ml of acetonitrile. Diaminobutane (2.7 ml, 25.4 mmol) is then added and the mixture is stirred at 50° C. under argon. After 5 hours, the solvent is evaporated off and the residue is taken up in ethyl acetate. This organic phase is washed with water saturated with NaCl. After drying over $Na_2SO_4$ and evaporation by chromatography on silica gel (eluent: $CH_2Cl_2$/MeOH: 8/2, then $CH_2Cl_2$/MeOH: 8/2 in the presence of 2% aqueous ammonia).

After evaporation, the product is obtained in the form of an oil (1 g, 2 mmol, 80%).

The aminated nucleoside was characterized by proton NMR, carbon 13 NMR and mass spectrometry.

Coupling to the Methyl Ketone Chain and Deprotection in 5'

6-Oxo-heptanoic acid (288 mg, 2 mmol) is dissolved in 5 ml of anhydrous THF. The solution is placed at 0° C. under argon. N-Methylmorpholine (223 p1, 2 mmol) is then added, followed by isobutyl dichloroformiate (258 µl; 2 mmol) 5 min later. After 15 minutes, the aminated nucleoside is added. After 2 hours, the THF is evaporated off and the residue is taken up with ether. This is washed with a 1 N aqueous NaOH solution and then with water saturated with NaCl. After drying over $Na_2SO_4$ and evaporation, an oil is obtained. The desilylation is carried out by taking the oil up in 10 ml of THF, to which TBAF (3.25 ml of a 1M solution in THF) is added. After one hour, the solvent is evaporated off. The residue is solubilized in dichloromethane and washing is carried out with water saturated with NaCl. After drying and evaporation, the residue is chromatographed on silica gel (eluent: $CH_2Cl_2$, then $CH_2Cl_2$/MeOH: 95/5).

After evaporation, 870 mg of the nucleoside carrying the methyl ketone function and deprotected in 5' (1.7 mmol, 85% over 2 steps) is obtained. It is carried by proton NMR, carbon 13 NMR and mass spectrometry.

Phosphorylation and Production of the Adenosine-(N6)—C10-Methyl Ketone Nucleotide 2

The adenosine-(N6)—C10-methyl ketone protected in 2', 3' by isopropylidene is dissolved in anhydrous pyridine and is evaporated twice. 500 µl of pyridine, 1.5 ml of dioxane and a freshly prepared solution of 2-chloro-4H-1,2,3-dioxaphosphain-4-one (1 M) in dioxane (650µl, 0.65 mmol) are then added under argon. Stirring is allowed to proceed for 20 minutes and then a 0.5 M solution of tributylammonium pyrophosphate in anhydrous DMF (1.6 ml, 0.8 mmol) is added simultaneously with 650 Ml of tributylamine.

After 30 minutes, 10 ml of 1% iodine solution is added to a pyridine/water (98/2, v/v) mixture. After 20 minutes, the excess iodine is destroyed with a 5% aqueous $NaHSO_3$ solution and stirring is maintained for 10 minutes, the mixture is evaporated to dryness and water/dichloromethane extraction is performed. The aqueous phase is evaporated off and then reverse phase (C18) purification is carried out (eluent: $H_2O$/MeOH). The fractions containing the product are evaporated and the counter-ion exchange is carried out by passing over Dowex, Na+ resin. The protected triphosphate (0.28 mmol, 56%) is thus recovered.

Deprotection 0.035 mmol of protected triphosphate are taken up in 17.5 ml of milli-Q water, to which 17.5 ml of a 25% aqueous TFA solution are added. The mixture is stirred for 15 minutes and then evaporated and coevaporated twice with water, and the product is taken up in 10 ml of milli-Q water and neutralized with 0.1 M sodium hydroxide, to pH 8. After evaporation, a C18 purification is carried out (eluent: $H_2O$; $H_2O$/MeOH). The fractions containing the product are evaporated and assayed. 0.022 mmol (63%) of the adenosine-(N6)-C10-methyl ketone triphosphate 2 are thus obtained-

I.3. Synthesis of Cytidine-(M4)—C10-Methyl Ketone

This nucleotide was prepared in two ways:

Nucleotide pathway: coupling between an activated ester of the methyl ketone chain and aminated cytidine triphosphate.

Nucleoside pathway: synthesis of the methyl ketone nucleoside then phosphorylation by the Eckstein method.

EXAMPLE II

Synthesis of the Oxyamine Fluorophore

II. 1. Synthetic Schemes

The oxyamine chain is introduced onto the fluorescein in three steps: the first step is nucleophilic addition of 1,3-diaminopropane to fluorescein isothiocyanate (FITC). After reverse phase purification, the oxyamine unit protected in the form of Fmoc is introduced by peptide coupling. The free oxyamine is generated by deprotection in basic medium.

4

Introduction of the 1.3-diaminoprogane Chain:

Diaminopropane (585 μl, 6.96 mmol) is added to 20 ml of anhydrous DMF. Fluorescein isothiocyanate (FITC) (500 mg, 1.16 mmol), solubilized in 7 ml of anhydrous DMF, is then added, dropwise, under argon. Stirring is maintained for 15 minutes after the FITC has been added. The mixture is evaporated to dryness and coevaporated twice with water. The residue is reverse phase (C18) chromatographed: (eluent: $H_2O$/MeOH: 1/1).

The product is thus recovered in the form of an orange powder (420 mg, 0.93 mmol, 80%). It is characterized by proton NMR, carbon 13 NMR and mass spectrometry.

Introduction of the Protected Alkoxyamine Group:

Carboxyalkoxyamine protected with Fmoc: HOOC—$CH_2$—ONH-Fmoc (473 mg, 1.5 mmol in 10 ml of anhydrous DMF) is solubilized. It is placed at 0° C. under argon. N-Methylmorpholine (166μl, 1.5 mmol) is then added and, after 15 minutes, the fluorescein carrying the diaminopropane chain (350 mg, 0.75 mmol) is added. After reacting for 1 hour, the DMF is evaporated off to dryness. The residue obtained is chromatographed on silica gel ($CH_2Cl_2$/MeOH: 85/15 (solid deposit)). The protected fluorescein-alkoxyamine is thus obtained in the form of an orange powder (227 mg, 0.3 mmol, 40%). It is characterized by proton NMR, carbon 13 NMR and mass spectrometry.

Production of the fluorescein-alkoxyamine Label 4:

The fluorescein protected with fmoc (100 mg, 0.13 mmol) is solubilized in 2 ml of anhydrous DMF. Pyridine (20μl, 0.2 mmol) is then added. After 15 minutes, the mixture is evaporated to dryness and then C118 reverse phase purification is carried out (eluent: $H_2O$/$CH_3CN$: 1/1 then $CH_3CN$). After evaporation, the product is obtained in the form of an orange powder (49 mg, 0.09 mmol, 70%). This fluorophore was characterized by proton NMR, 13C NMR and mass spectrometry.

EXAMPLE III

Reactivity of the Methyl Ketone Compounds with the Fluorophore

The reactivity was tested at the nucleoside level and at the nucleotide level:

R = OH, triphosphate

The reaction is carried out in the presence of 1.1 eq. of fluorophore-$ONH_2$ (4) with respect to the methyl ketone compound. The reaction is rapid and selective. At the nucleoside level, the adducts were characterized by proton NMR and mass spectrometry.

EXAMPLE IV

Incorporation of the Uridine-Methyl Ketones and Post-Transcription Labeling

IV.1. Description of the Main Steps

Transcriptions

The transcriptions were carried out on a PCR target (fragment of the 16 S RNA of Mycobacterium tuberculosis (Mtb)) (Troesch A. et al, J. Clin. Microbiol., 37(1), 49–55, 1999) or a fragment of HIV reverse transcriptase (Kozal M. J. et al, Nature Medecine, 2(7), 753–759, 1996) using T7 RNA polymerase and various ratios between the functionalized nucleotide and the natural nucleotides, while at the same time keeping the total concentration of each nucleotide at 1 mM. This ratio between the functionalized nucleotide and the corresponding natural nucleotide is expressed as a percentage and the ratios used are in general 0, 30, 70 and 100%. The point 0% is used as a transcription control since, in this case, there is no functionalized nucleotide and the transcription reaction comprises the 4 natural nucleotides. When the ratio is 100%, this means that the functionalized nucleotide represents 100% of the nucleotide studied (the other three nucleotides required for the transcription reaction naturally being the natural nucleotides). This ratio of 100% for a functionalized nucleotide is the most significant test of the neutrality with respect to an enzymatic reaction since the enzyme must incorporate this nucleotide in order to function correctly. The incubation time for the transcription reaction is 1 h at 42° C.

The transcriptions are analyzed by polyacrylamide gel electrophoresis under denaturing conditions (6% acrylamide, 7 M urea, 1×TBE). The volume loaded is 5 $\mu$l and the migration takes place for 45 min at 150 V. The transcripts, natural or functionalized with the methyl ketone function, are visualized under a UV lamp after staining with ethidium bromide.

Assay

The amount of transcripts produced in each reaction is determined by UV assay, after purification, of an aliquot derived from a transcription reaction.

Enzymatic Digestion

The transcripts are purified on microcon-50 filters (Amicon, Beverly, Mass.) in order to remove the excess of unincorporated nucleotides. They are then hydrolyzed according to the protocol described in patent application WO 98/05766 using P1 nuclease (Boehringer reference 2362251,2U, 2 h at 37° C.) and alkaline phosphatase (Boehringer-Mannheim reference 713023, 1U, 1 h at 37° C.). The digestions are carried out on $4\times10^{14}$ transcript copies. The nucleoside composition is determined by reverse phase HPLC, by comparing with nucleoside standards composed of a mixture of natural nucleosides.

The HPLC conditions are as follows:
analytical C18 column (250×4.6 mm) heated to 450° C.,
eluents: A: 50 mM sodium phosphate buffer, pH 7; B: MeOH/$H_2O$: 95/5, v/v
gradient: 0% of B for 10 min, up to 30% of B in 10 min, up to 80% of B in 10 min, 5 min at 80% of B, up to 100% of B in 2 min.

Labeling

The transcripts are labeled using various proportions of fluorophore. The reaction time is 30 min at room temperature. The labeling is carried out on the transcripts generated from an Mtb target and/or HIV target, obtained by incorporation of 100% of a methyl ketone nucleotide. Initially, the labeled transcripts are analyzed by polyacrylamide gel electrophoresis and visualized under UV, before and after staining with ethidium bromide.

Cleavage

Before hybridizing on the DNA chip, the labeled transcripts are cleaved at ~65° C. for 30 min using imidazole and manganese chloride ($MnCl_2$) each at a concentration of 30 mM.

Hybridization on a DNA Chip

After cleavage, the fragments obtained are hybridized, detected and analyzed on a DNA chip (Affymetrix, Santa Clara, Calif., USA) according to the protocol supplied by the manufacturer.

The "myco" chips are designed for resequencing the 213–415 region of the "Genbank" M20940 sequence of the 16S RNA of *Mycobacterium tuberculosis* (Troesch A. et al, J. Clin. Microbiol., 37(1), 49–55, 1999). Those termed "HIV PRT 440" are designed for resequencing the RT (reverse transcriptase) and protease regions of the HIV virus (Kozal M. J. et al, Nature Medecine, 2(7), 753–759, 1996).

In the case of the Mtb transcript, $10^{14}$ copies are hybridized on the chip.

In the case of the HIV transcript, $5\times10^{12}$ copies are hybridized on the chip.

IV. 2. Results

Incorporation of the uridine(C5)—C9-methyl Ketone Nucleotide 1 (U—$COCH_3$)

| Target used | Ratio between functionalized nucleotide U—$COCH_3$ and natural nucleotide | Transcripts produced (copies/microliters) |
|---|---|---|
| Mtb | 0% | $5.0^E + 13$ |
|  | 30% | $5.0^E + 13$ |
|  | 70% | $3.0^E + 14$ |
|  | 100% | $0.8^E + 14$ |
| HIV | 0% | $0.9^E + 12$ |
|  | 70% | $0.9^E + 12$ |
|  | 100% | $0.9^E + 12$ |

The results in the table above show that the uridine-methyl ketone nucleotide (1) is very well incorporated by T7 RNA polymerase. This allows the production of activated transcripts capable of reacting with a label carrying the alkoxyamine function.

Evaluation of the Incorporation by HPLC

The peak which corresponds to the U-methyl ketone nucleoside (retention time 26.2 minutes) is indeed observed in the chromatographic profile of the hydrolyzate of the transcripts containing 100% of U-$COCH_3$ (1) and obtained from the Mtb target, which means that the nucleotide is not modified during the transcription and enzymatic digestion steps. The absence of the peak corresponding to the natural uridine (retention time 14.97 minutes) is also noted.

This shows that the U-methyl ketone nucleotide is correctly incorporated and can be used at 100% in a transcription reaction.

Evaluation of the Labeling by Polyacrylamide Gel

The labeling was carried out on the crude transcripts generated from an Mtb target, using 100% of the U-$COCH_3$ nucleotide (1). The amount of fluorophore compared to the number of reactive sites was varied. These ratios are: 2, 5, 10, 15, 20 and 50 equivalents of flurophore-$ONH_2$. 10 equivalents are suitable for intensive and selective labeling.

On a gel, before staining with ETB, representing labeling using 5, 10 and 15 eq. of the fluorophore, labeling is observed which is more or less intense depending on the number of equivalents of fluorophore used, but there is a visible band whatever the amount of labels used. The appearance of new bands is also noted at high doses of fluorophore. This is certainly due to a high density of the label on the target.

Hybridization and Analysis of the Results

The Mtb and HIV transcripts generated from corresponding targets, using 100% of UTP-COCH$_3$ (1), underwent the treatments described above. During the cleavage step, a "blocking" agent (acetone or glutaraldehyde) was used in order to avoid saturating the chip with the excess of fluorophore-ONH$_2$ which adsorbs to the surface of this chip. The hybridization is carried out using the "Gene Chip fluidics Station" for hybridization (800101 Affymetrix, Santa Clara, Calif.), the suitable chips and buffers and the protocol supplied by the manufacturer.

The base call percentage, mean signal intensity, median intensity and background noise parameters were calculated using the software provided by the manufacturer (GenChip sequence analysis system, reference 900135, Affymetrix, Santa Clara, Calif.). The results are given in the two tables below. The signal intensity is expressed in RFU (fluorescence units of the manufacturer)

Mtb Transcripts:

| Target | Base call (%) | Mean intensity (Rfu) | Median intensity (Rfu) |
|---|---|---|---|
| *Mycobacterium tuberculosis* 100% U-COCH$_3$ transcripts | | | |
| 100 eq Fluo-ONH$_2$ + 100 eq acetone | 97.7 | 3540 | 3260 |
| 20 eq Fluo-ONH$_2$ + 20 eq glutaraldehyde | 92.4 | 12630 | 11970 |

Base call: percentage of bases correctly identified.

HIV Transcripts

| Target | Base call (%) | Mean intensity (Rfu) | Median intensity (Rfu) |
|---|---|---|---|
| HIV | | | |
| 70% U-COCH$_3$ transcripts 10 eq Fluo-ONH$_2$ + 10 eq glutaraldehyde | 98.8 | 2175 | 1765 |
| 100% U-COCH$_3$ transcripts 10 eq Fluo-ONH$_2$ + 10 eq glutaraldehyde | 99.0 | 2675 | 2090 |
| 100% U-COCH$_3$ transcripts 5 eq Fluo-ONH$_2$ without blocking | 97.5 | 4750 | 4095 |
| 100% U-COCH$_3$ transcripts 5 eq Fluo-ONH$_2$ + 5 eq glutaraldehyde | 98.5 | 1825 | 1550 |
| 100% U-COCH$_3$ transcripts 2 eq Fluo-ONH$_2$ without blocking | 98.3 | 2380 | 2035 |
| 100% U-COCH$_3$ transcripts 2 eq Fluo-ONH$_2$ + 2 eq glutaraldehyde | 98.8 | 620 | 540 |

In both the Mtb and HIV cases, very effective labeling with intensities greater than 1000 Rfu and resequencing (base call) percentages close to 100% are observed. These results show that the reaction between the alkoxyamine and methyl ketone, demonstrated at the monomer stage, is therefore specific and effective between RNA sequences containing methyl ketone functions and the fluorescent label carrying the alkoxyamine function. Specifically, a sufficient amount of labeled and detectable transcript fragments are obtained with only 2 equivalents of alkoxyamine label per methyl ketone function.

EXAMPLE V

Incorporation of the Cytidine-Methyl Ketone 3 and Post-Transcription Labeling

The cytidine 3 was incorporated at 100% into RNAs transcribed from Mtb, as described in Example III. The cleavage and labeling method is also carried out as indicated above.

| Target | Base call (%) | Mean intensity (Rfu) | Median Intensity (Rfu) |
|---|---|---|---|
| 100% C—COCH$_3$ transcripts 20 eq Fluo—ONH$_2$ + 20 eq glutaraldehyde | 94.2 | 6655 | 6200 |

Here again, very effective labeling is observed. The signal intensity is greater than 6000 Rfu and the resequencing is 94%. As in the previous example, this result demonstrates that the reaction between the alkoxy-amine and methyl ketone is specific and effective between RNA sequences containing methyl ketone functions and the fluorescent label carrying the alkoxyamine function.

EXAMPLE VI

Advantages of the Methyl Ketone Function Compared to Alkoxyamine, Aldehyde and Amine Functions.

1. Comparison Between the Alkoxyamine and Methyl Ketone Function on the U Nucleotide.

Uridine carrying an alkoxyamine chain at position is prepared according to the method described in Example 4 of patent application WO-A-98/05766. The synthesis of the fluorescein aldehyde (FLUO-CHO) label is described in Example 18 of application WO-A-98/05766.

It is important to note that the alkoxyamine function requires permanent protection with the tert-butoxycarbonyl (BOC) group. This function is deprotected at the same time as the isopropylidene in 2',3' after phosphorylation in the presence of 50% trifluoroacetic acid. This percentage of TFA is necessary to obtain a deprotection of the alkoxyamine close to 90%. In order to obtain total deprotection, more concentrated acid solutions are necessary. In these solutions, the triphosphate degrades very rapidly to diphosphate and monophosphate.

In the case of the methyl ketone function, no deprotection is necessary and only 25% of TFA is used for total deprotection of the isopropylidene in 2',3' after phosphorylation. No degradation is observed with this percentage of TFA.

The methyl ketone chain is sufficiently hydrophobic even after deprotection; it thus contributes to good separation of the nucleotide triphosphate when it is purified by reverse phase HPLC. This separation is more difficult in the case of the alkoxyamine chain.

Incorporation and Post-Labeling of the UTP-Alkoxyamine

The reactions for transcription, enzymatic hydrolysis of the transcripts, HPLC analysis and post-labeling are carried out under the same conditions as those described in Example IV.

Figure 1:
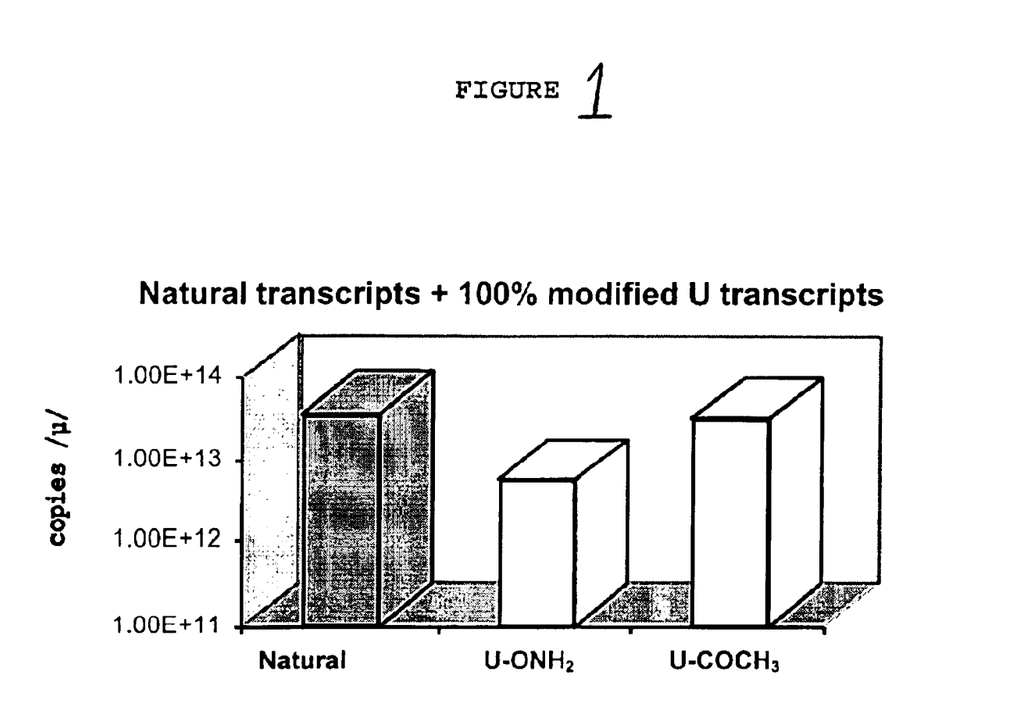

The FIGURE shows the transcription yields measured in terms of the amount of amplicons produced (on the y-axis in copies/microliters) as a function of the 3 nucleotides used.

In this example, the incorporation of the two nucleotides, alkoxyamine (U-ONH$_2$) and methyl ketone (U-COCH$_3$ compound 1), is studied.

The uridine-methyl ketone 1 at 100% has no effect on the transcription yield. This yield is lower when the same nucleotide carrying the alkoxyamine function is incorporated.

Post-labeling:

| MTB TARGET | Base call (%) | Mean intensity (Rfu) | Median intensity (Rfu) |
|---|---|---|---|
| 100% U—ONH$_2$ TRANSCRIPTS + 10 EQ FLUO—CHO | 91.6 | 5735 | 5335 |

The resequencing percentage using the uridine-alkoxyamine is lower than that obtained with its homolog carrying the methyl ketone function.

2. Comparison Between the Aldehyde and Methyl Ketone Function on the U Nucleotide.

The uridine with an aldehyde chain (U—CHO) is prepared according to the following scheme:

The chain is synthesized by peptide coupling between 4-aminobutyraldehyde diethylacetal and 4-pentynoic acid. Heck coupling produces the protected nucleoside. Phosphorylation followed by deprotection in acid medium correctly produces the expected nucleotide. The products were characterized by $^1$H NMR and $^{13}$C NMR.

Here again, it is necessary for the aldehyde function to be protected during the coupling and phosphorylation steps. The deprotection of the aldehyde is carried out at the same time as that of the isopropylidene (25% of TFA); however, the purification and desalination of the deprotected product are more difficult compared to those of the nucleotide-methyl ketone (U—COCH$_3$, compound 1). The yield from the phosphorylation step is 20%.

The HPLC analysis of the transcripts containing the UTP-aldehyde, hydrolyzed using the enzymatic technique described in Example IV, shows that the nucleotide-aldehyde is transformed. This transformation is certainly due to the aldehyde function interacting with components of the buffers during the transcription or enzymatic hydrolysis of the transcripts.

The post-labeling reaction using the fluorescein-alkoxyamine shows no result after analysis of the mycobacterium transcripts on gel and on DNA chips. This shows that transformation of the aldehyde has occurred during the transcription step, which shows the advantage of the methyl ketone function compared to the aldehyde.

3. Comparison between the Amine and Methyl Ketone Function on the U Nucleotide.

The uridine carrying an amine chain at position 5 (U-NH$_2$) is prepared according to the method described in Example 3 of patent application WO 98/05766. It is necessary to protect the amine function with the Boc group in this case as well.

The transcription yields obtained with 100% of U-NH$_2$ are much lower than when the methyl ketone function is used and do not allow efficient resequencing on the DNA chip both in the case of Mtb and in the case of HIV.

4. Comparison Between the Amine and Methyl Ketone Function on the C Nucleotide.

The cytidine carrying an amine chain at position 4 (C—NH$_2$) is prepared according to Example 16 of patent application WO-A-98/05766.

This nucleotide was incorporated into fragments of the 16S RNA of *Mycobacterium tuberculosis* through transcription reactions carried out on a PCR target according to the protocol described in Example IV.

The HPLC analysis of the transcripts containing the C—NH$_2$, hydrolyzed using the enzymatic technique described in the example above, shows that the aminated nucleotide is correctly incorporated and is intact.

The yields from transcription with various percentages of C—NH$_2$, also determined as indicated in Example IV, are given in the table below.

| Ratio between functionalized nucleotide C—NH$_2$ and natural nucleotide (%) | Transcripts produced (copies/microliters) |
|---|---|
| 0 | 3.48$^E$ + 13 |
| 70 | 1.94$^E$ + 13 |
| 100 | 1.51$^E$ + 12 |

It is important to note that, with 100% of C—NH$_2$, the amount of amplicons obtained is 20 times less than that obtained with transcription containing 100% of natural nucleotide.

The labeling reagent used in the post-labeling reaction was fluorescein isothiocyanate obtained from Sigma-Aldrich (St Quentin Falavier, France).

Fluorescein isothiocyanate (FITC)

The labeling of the transcripts obtained by incorporation of the C—NH$_2$ were labeled with FITC, hybridized on the DNA chip intended for the identification of these Mtb targets, and the signals were analyzed according to the protocol described above. The results obtained with and without blocking agent are given in the table above

| Target | Base call (%) | Mean intensity (Rfu) |
|---|---|---|
| Nonpurified transcripts + 100 eq FITC | ND | ND |
| Nonpurified transcripts + 100 eq FITC + 1000 eq of blocking diamine | 86 | 346 |

ND : not determined, the surface of the chip is completely saturated.
Blocking diamine : H$_2$N—CH$_2$—CH$_2$—O—CH$_2$—CH$_2$—O—CH$_2$—CH$_2$—NH$_2$.

If the diamine chain is not added after the labeling, the surface of the chip is completely saturated with the 100 eq of label and the signals cannot be exploited. This saturation is certainly due to the interaction of the isothiocyanate function with the exocyclic amine functions of the bases.

The post-labeling addition of 1000 eq of diamine, having the same structure as that carried by the cytidine, appears to confirm this hypothesis since the surface of the chip is no longer saturated, and 86% resequencing is obtained. The signal intensity is low compared to that obtained with transcripts containing the methyl ketone and labeled with fluorescein-alkoxyamine.

In addition to the inhibitory effect of the C-NH$_2$ during the transcription, the resequencing percentage when the C-NH$_2$ is used is lower than that obtained with its homolog carrying the methyl ketone function (C-COCH$_3$, compound 3).

What is claimed is:

1. Functionalized compound of general formula (I):

in which:

W represents a nucleotide or nucleoside, or an analog of a nucleotide or nucleoside, L represents a linker arm comprising a chain of at least four atoms in series, and L is a saturated or unsaturated hydrocarbon-based chain, optionally interrupted by at least one function chosen from amine, amide and oxy functions, and is grafted onto any position of a nitrogen-containing base of the nucleotide or nucleoside of W, and

R$_1$ represents a linear or branched alkyl chain.

2. Compound according to claim 1, characterized in that R1 represents an alkyl chain having at most 6 carbon atoms.

3. Compound according to claim 2, characterized in that R1 represents a methyl group.

4. Compound according to claim 1, characterized in that L comprises a chain of at least eight atoms in series.

5. Compound according to claim 1, characterized in that W corresponds to the general formula (II)

in which:

B represents a nitrogen-containing base,

R$_2$ represents H or a protective group,

R₃ represents H, F, OH, SH, NH₂, OCH₃ or OR₅ in which R₅ represents a protective group or an alkyl chain, and R₄ represents an H radical, a protective group or a mono-, di- or triphosphate group, W being attached to L via B.

6. Compound according to claim 5, characterized in that the nitrogen-containing base is cytosine, uracil or adenine.

7. Compound according to claim 5, characterized in that R₂ is an H, R₃ is an OH group and R₄ is a triphosphate group.

8. Compound according to claim 5, characterized in that R₂ is a 2-cyanoethyl-N,N-diisopropylphosphoramidite group and R₃ is H or OR₅ in which R₅ is a protective group used in oligoribonucleotide synthesis and R₄ is a 4,4'-dimethoxytrityl group.

9. Functionalized polynucleotide comprising at least one functionalized compound according to claim 1.

10. Functionalized polynucleotide according to claim 9, characterized in that this polynucleotide is prepared by a chemical and/or enzymatic route.

11. Functionalized polynucleotide according to claim 10, characterized in that this polynucleotide is prepared using an enzymatic amplification reaction.

12. Labeled functionalized polynucleotide, characterized in that it comprises at least one functionalized compound of general formula (I'):

W-[-L-]ₙ—CH₂COR₁    (I')

in which:

W represents a nucleotide or nucleoside, or an analog of a nucleotide or nucleoside, L represents a linker arm comprising at least four atoms, and L is a saturated or unsaturated hydrocarbon-based chain, optionally interrupted by at least one function chosen from amine, amide and oxy functions, and is grafted onto any position of a nitrogen-containing base of the nucleotide or nucleoside of W, n represents an index equal to 0 or 1, and R₁ represents a linear or branched alkyl chain, the alkyl ketone group of said functionalized compound being attached to a labeling reagent.

13. Polynucleotide according to claim 12, characterized in that R₁ represents an alkyl chain having at most 6 carbon atoms.

14. Polynucleotide according to claim 13, characterized in that R₁ represents a methyl group.

15. Polynucleotide according to claim 12, characterized in that L comprises at least eight atoms.

16. Polynucleotide according to claim 12, characterized in that W corresponds to the general formula (II)

in which:

B represents a nitrogen-containing base,

R₂ represents H or a protective group,

R₃ represents H, F, OH, SH, NH₂, OCH₃ or OR₅ in which R₅ represents a protective group or an alkyl chain, and R₄ represents an H radical, a protective group or a mono-, di- or triphosphate group, W being attached to L via B.

17. Polynucleotide according to claim 16, characterized in that the nitrogen-containing base is cytosine, uracil or adenine.

18. Polynucleotide according to claim 16, characterized in that R₂ is an H, R₃ is an OH group and R4 is a triphosphate group.

19. Compound according to claim 16, characterized in that R₂ is a 2-cyanoethyl-N,N-diisopropylphosphoramidite group and R₃ is H or OR₅ in which R₅ is a protective group used in oligoribonucleotide synthesis and R4 is a 4,4'-dimethoxytrityl group.

20. Polynucleotide according to claim 12, characterized in that the labeling reagent comprises a hydrazine or alkoxyamine function.

21. Polynucleotide according to claim 20, characterized in that the labeling reagent is:

22. Method for detecting a target nucleic acid, characterized in that this target nucleic acid is brought into contact with at least one functionalized nucleotide as defined in claim 12, in the presence of elements and under conditions required for producing a polynucleotide, so as to produce a functionalized polynucleotide; the polynucleotide obtained is labeled with a labeling reagent; and then said labeled polynucleotide is detected.

23. Method according to claim 22, characterized in that the functionalized polynucleotide is obtained using an enzymatic amplification reaction.

24. Method for detecting a target nucleic acid, characterized in that this target nucleic acid is brought into contact with a functionalized polynucleotide according to claim 9; the labeling reagent is reacted; and the presence of the target nucleic acid is detected.

25. Method for detecting a target nucleic acid, characterized in that a labeled polynucleotide according to claim 12 is available for use, this target nucleic acid is brought into contact with the labeled polynucleotide; and the presence of the target nucleic acid is detected.

26. Compound according to claim 4, characterized in that L contains a chain of 8 to 30 atoms in series.

27. Polynucleotide according to claim 15, characterized in that L contains a chain of 8 to 30 atoms in series.

28. Compound according to claim 1, wherein said linker atom comprises at least 4 carbon atoms.

* * * * *